US00PP15632P2

(12) United States Plant Patent
Sorensen

(10) Patent No.: US PP15,632 P2
(45) Date of Patent: Mar. 8, 2005

(54) ***OSTEOSPERMUM* PLANT NAMED 'IRINGA'**

(50) Latin Name: *Osteospermum ecklonis*
Varietal Denomination: Iringa

(75) Inventor: Carl Aksel Kragh Sorensen, Aabyhoj (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/820,512

(22) Filed: Apr. 7, 2004

(51) Int. Cl.[7] ..... A01H 5/00
(52) U.S. Cl. ..... Plt./360
(58) Field of Search ..... Plt./360

(56) References Cited

U.S. PATENT DOCUMENTS

PP10,603 P * 9/1998 Kanno ..... Plt./360

OTHER PUBLICATIONS

UPOV ROM GTITM Computer Database, GTI Jouve Retrieval Software 2004/02 Citation for 'Iringa'.* http://www.greenbeam.com/features/tour060903k.stm.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Osteospermum* plant named 'Iringa', characterized by its uniformly mounded plant habit; freely branching growth habit; full and dense plants; freely flowering habit; dark green-colored foliage; large inflorescences with dark red purple-colored ray florets; and high temperature tolerance.

1 Drawing Sheet

Botanical classification/cultivar designation: *Osteospermum ecklonis* cultivar Iringa.

BACKGROUND OF THE INVENTION

The present Invention relates to a new and distinct cultivar of *Osteospermum* plant, botanically known as *Osteospermum ecklonis,* and hereinafter referred to by the name 'Iringa'.

The new *Osteospermum* is a product of a planned breeding program conducted by the Inventor in Aabyhøj, Denmark. The objective of the breeding program is to create new *Osteospermum* cultivars with uniform plant habit, interesting floret colors and high temperature tolerance.

The new *Osteospermum* originated from a cross-pollination made by the Inventor during the spring of 1999 of a proprietary selection of *Osteospermum ecklonis* identified as code number 98038, not patented, as the female, or seed, parent with the *Osteospermum ecklonis* cultivar Lubango, not patented, as the male, or pollen, parent. The new *Osteospermum* was discovered and selected by the Inventor as a single flowering plant within the progeny of the stated cross-pollination grown in a controlled environment in Aabyhøj, Denmark during the spring of 2000.

Asexual reproduction of the new *Osteospermum* by vegetative tip cuttings was first conducted in Aabyhøj, Denmark in February, 2000. Asexual reproduction by cuttings has shown that the unique features of this new *Osteospermum* are stable and reproduced true to type in successive generations.

SUMMARY OF THE INVENTION

The cultivar Iringa has not been observed under all possible environmental conditions. The phenotype may vary somewhat with variations in environment such as temperature and light intensity without, however, any variance in genotype.

The following traits have been repeatedly observed and are determined to be the unique characteristics of 'Iringa'. These characteristics in combination distinguish 'Iringa' as a new and distinct *Osteospermum:*

1. Uniformly mounded plant habit.
2. Freely branching growth habit; full and dense plants.
3. Freely flowering habit.
4. Dark green-colored foliage.
5. Large inflorescences with dark red purple-colored ray florets.
6. High temperature tolerance.

Plants of the new *Osteospermum* have larger inflorescences than plants of the female parent selection. In addition, plants of the new *Osteospermum* and the female parent selection differ in ray floret coloration as plants of the female parent selection have dark blue purple-colored ray florets. Compared to plants of the male parent, the cultivar Lubango, plants of the new *Osteospermum* grow faster, have darker green-colored leaves and darker red purple-colored ray florets.

The new *Osteospermum* can be compared to plants of the cultivar Wildside, disclosed in U.S. Plant Pat. No. 10,603. In side-by-side comparisons conducted in Aabyhøj, Denmark, plants of the new *Osteospermum* differed from plants of the cultivar Wildside in the following characteristics:

1. Plants of the new *Osteospermum* had narrower leaves than plants of the cultivar Wildside.
2. Plants of the new *Osteospermum* had larger inflorescences than plants of the cultivar Wildside.

3. Ray florets of plants of the new *Osteospermum* were darker red purple in color than ray florets of plants of the cultivar Wildside.
4. Plants of the new *Osteospermum* had shorter peduncles than plants of the cultivar Wildside.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum.*

The photograph at the top of the sheet comprises a side perspective view of a typical flowering plant of 'Iringa' grown in container.

The photograph at the bottom of the sheet is a close-up view of typical leaves, inflorescence buds and inflorescences of 'Iringa'.

DETAILED BOTANICAL DESCRIPTION

In the following description, color references are made to The Royal Horticultural Society Colour Chart, 1995 Edition, except where general terms of ordinary dictionary significance are used.

The aforementioned photographs, following observations and measurements describe plants grown during the late winter and early spring in Encinitas, Calif., in a polyethylene-covered greenhouse and under conditions which approximate those generally used in commercial *Osteospermum* production. Single plants were grown in one-gallon containers and pinched once. During the production of the plants, day temperatures were about 24° C., night temperatures were about 19° C., and light levels were about 4,000 foot-candles. Measurements and numerical values represent averages of typical flowering plants about 20 weeks after planting.

Botanical classification: *Osteospermum ecklonis* cultivar Iringa.

Parentage:

*Female, or seed, parent.*—Proprietary selection of *Osteospermum ecklonis* identified as code number 98038, not patented.

*Male, or pollen, parent.*—*Osteospermum ecklonis* cultivar Lubango, not patented.

Propagation:

*Type.*—Terminal cuttings.

*Time to initiate roots, summer.*—About 10 days at 18° C.

*Time to initiate roots, winter.*—About 12 days at 18° C.

*Time to develop roots, summer.*—About 22 days at 18° C.

*Time to develop roots, winter.*—About 24 days at 18° C.

*Root description.*—Fibrous, fine; white in color.

*Rooting habit.*—Freely branching.

Plant description:

*Appearance.*—Perennial herbaceous container and garden plant. Uniformly mounded plant habit; upright and somewhat outwardly spreading; inverted triangle. Freely branching, about eight primary lateral branches each with about three or four secondary lateral branches; dense and full plants. Vigorous growth habit.

*Plant height.*—About 48 cm.

*Plant width or area of spread.*—About 64 cm.

*Lateral branches.*—Length: About 35 cm. Diameter: About 7 mm. Internode length: About 1.5 cm. Aspect: Initially upright then bending outwardly. Strength: Strong. Texture: Glabrous, smooth. Color: 144A.

*Foliage description.*—Arrangement: Alternate; simple. Length: About 6.5 cm. Width: About 2.8 cm. Shape: Roughly oblanceolate. Apex: Broadly acute. Base: Attenuate. Margin: Coarsely dentate. Venation pattern: Pinnate. Texture, upper and lower surfaces: Slightly rough, leathery, glandular and glabrous. Color: Developing and fully expanded foliage, upper surface: 147A. Developing and fully expanded foliage, lower surface: 147B. Venation, upper surface: 147C. Venation, lower surface: 146C. Petiole: Length: About 2.2 cm. Diameter: About 7 mm. Texture, upper and lower surfaces: Glabrous. Color, upper and lower surfaces: 146D.

Inflorescence description:

*Appearance.*—Terminal and axillary inflorescences held above and beyond the foliage. Composite inflorescence form, radially symmetrical, with ligulate-shaped ray florets and disc florets massed at the center; ray and disc florets arranged acropetally on a capitulum. Inflorescences face upright or outwardly.

*Flowering response.*—Plants flower continuous and freely from the spring through the fall.

*Postproduction longevity.*—Inflorescences maintain good color and substance for about ten days on the plant when grown in an outdoor environment. Inflorescences persistent.

*Quantity of inflorescences.*—Freely flowering; more than 250 open inflorescences and inflorescence buds per plant.

*Fragrance.*—None detected.

*Inflorescence bud* (*at stage of showing color*).—Length: About 1.3 cm. Diameter: About 8 mm. Shape: Ovoid. Color: 77A.

*Inflorescence size.*—Diameter: About 6.2 cm. Depth (height): About 2 cm. Disc diameter: About 9 mm. Receptacle diameter: About 1.3 cm. Receptacle height: About 1 cm.

*Ray florets.*—Length: About 3.4 cm. Width: About 8 mm. Shape: Ligulate. Apex: Emarginate. Base: Attenuate. Margin: Entire. Texture, upper and lower surfaces: Smooth; velvety. Orientation: Initially 30 to 45° from vertical, with development, close to 90° from vertical. Number of ray florets per inflorescence: About 19 in a single whorl. Color: When opening, upper surface: 71A. When opening, lower surface: Ground color, 77A; longitudinal stripes, 79B. Fully opened, upper surface: Alternating longitudinal stripes of 71A and 71B. Fully opened, lower surface: Alternating longitudinal stripes of 79B and more gray than 77B.

*Disc florets.*—Shape: Tubular, elongated. Apex: Five-pointed. Length: About 8 mm. Width: At apex: About 2 mm. At base: Less than 1 mm. Number of disc florets per inflorescence: About 80. Color: Immature: 79A. Mature: Apex: 79A. Mid-section: 77A. Base: 79D.

*Phyllaries.*—Length: About 8 mm. Diameter: About 1 mm. Shape: Linear. Apex: Acuminate. Base: Fused. Margin: Entire. Texture, upper and lower surfaces: Slightly pubescent. Number per inflorescence: About 18 in a single whorl. Color, upper and lower surfaces: 144A.

*Peduncles.*—Length, terminal peduncle: About 10.7 cm. Length, second peduncle: About 12 cm. Length, third peduncle: About 12.5 cm. Diameter: About 2 mm. Angle: Terminal peduncles, erect; secondary and tertiary peduncles, about 30 to 45° from vertical. Strength: Strong. Texture: Coarse with tiny scattered short hairs; glandular. Color: 144A.

*Reproductive organs.*—Androecium: Present on disc florets only. Stamen number: Five per floret; fused around style. Anther shape: Oblong. Anther length: Less than 1 mm. Anther color: 79A. Pollen amount: Scarce. Pollen color: 23A. Gynoecium: Present on both ray and disc florets. Pistil number: One per floret. Pistil length: About 7 mm. Stigma shape: Two-parted. Stigma color: 79A. Style length: About 4 mm. Style color: 79A. Ovary color: 157A.

*Seed/fruit.*—Seed and fruit production has not been observed.

Disease/pest resistance: Resistance to pathogens and pests common to *Osteospermums* has not been observed on plants grown under commercial greenhouse or outdoor conditions.

Temperature tolerance: Plants of the new *Osteospermum* have been observed to tolerate temperatures from 0 to 40° C.

It is claimed:

1. A new and distinct cultivar of *Osteospermum* plant named 'Iringa', as illustrated and described.

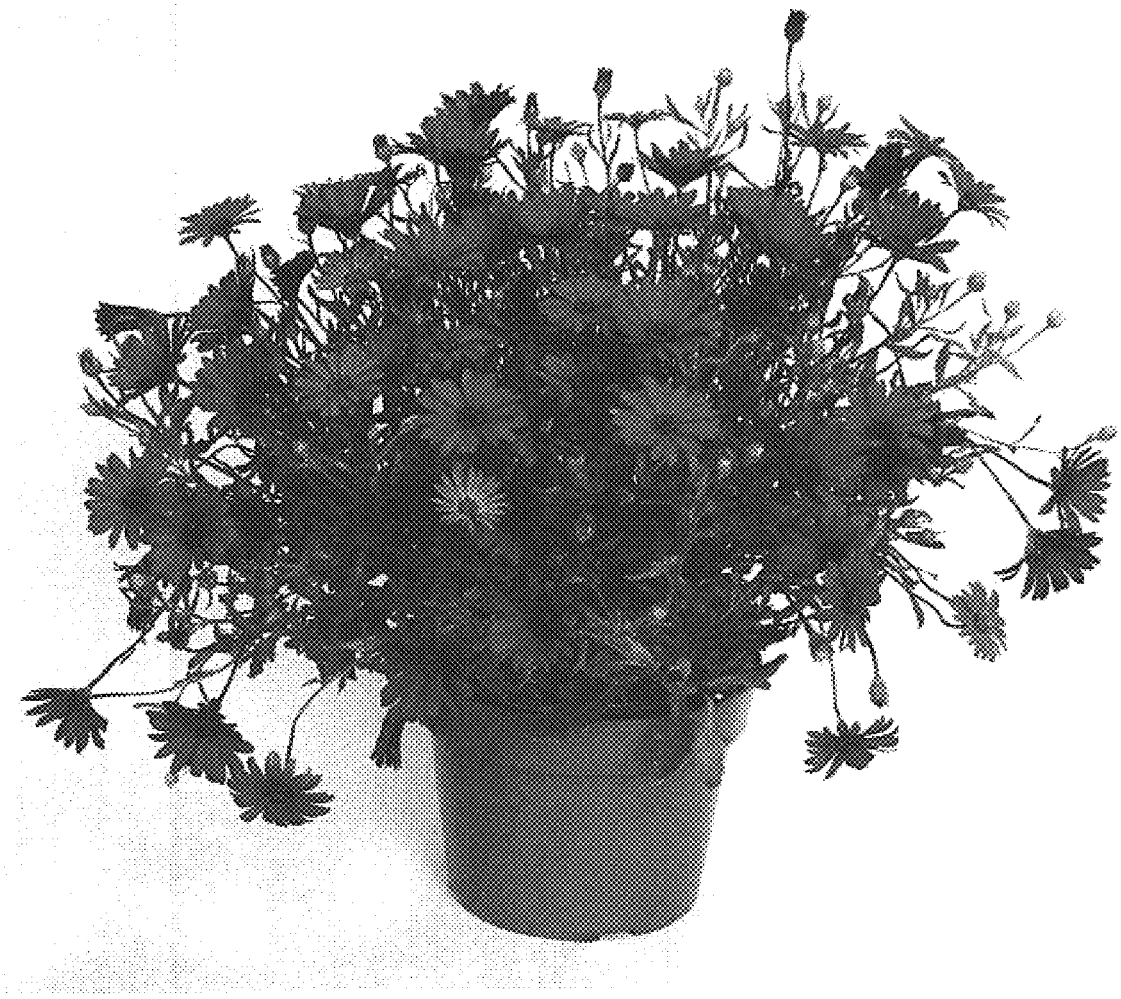
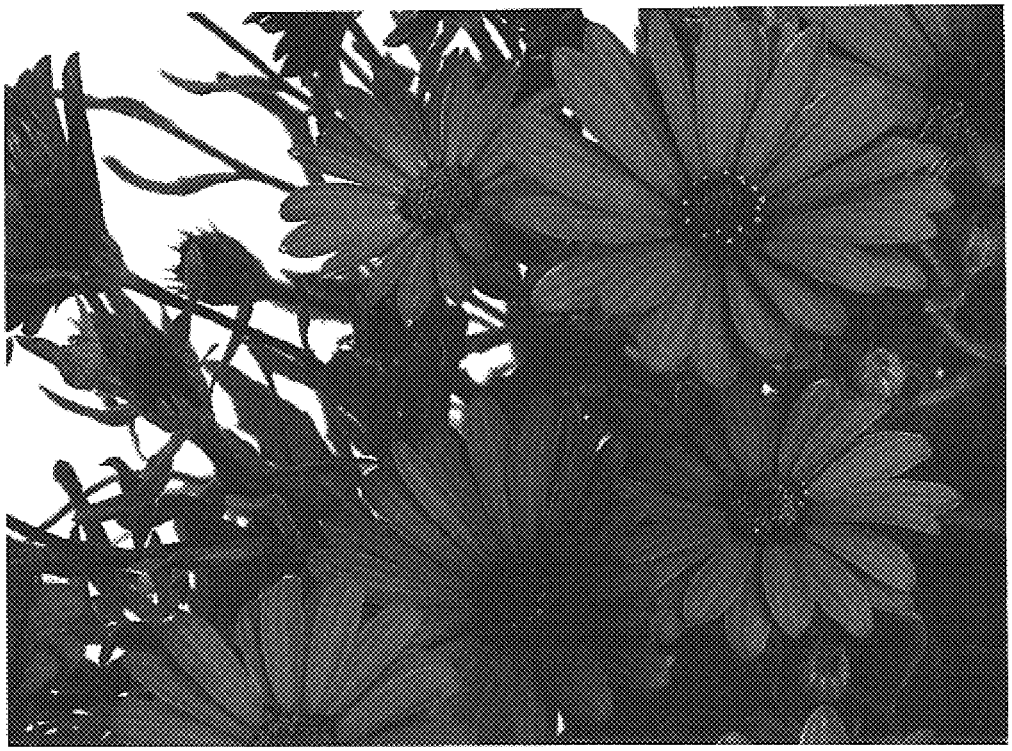

* * * * *